United States Patent
D'Angelo

(10) Patent No.: US 7,387,899 B1
(45) Date of Patent: Jun. 17, 2008

(54) SALIVA SAMPLE COLLECTION SYSTEM

(76) Inventor: Joseph P. D'Angelo, 20 NW. 181st St., Miami, FL (US) 33169

( * ) Notice: Subject to any disclaimer, the term of this patent is extended or adjusted under 35 U.S.C. 154(b) by 1765 days.

(21) Appl. No.: 08/500,535

(22) Filed: Jul. 11, 1995

(51) Int. Cl.
G01N 1/10 (2006.01)
G01N 21/03 (2006.01)
C12M 1/30 (2006.01)
C12M 1/28 (2006.01)
B01L 11/00 (2006.01)

(52) U.S. Cl. .................... 436/178; 422/58; 422/101; 435/287.7; 435/309.1; 436/164; 436/165

(58) Field of Classification Search ............. 128/760, 128/762, 769; 422/56, 58, 101; 435/294, 435/295, 287.7, 309.1; 436/164–165, 178; 119/709–710; 374/151; 606/234–236; 600/573
See application file for complete search history.

(56) References Cited

U.S. PATENT DOCUMENTS

| | | | | | |
|---|---|---|---|---|---|
| 3,610,248 | A | * | 10/1971 | Davidson | 606/236 |
| 3,682,321 | A | * | 8/1972 | Smith | 422/101 X |
| 3,682,596 | A | * | 8/1972 | Stone | 422/101 X |
| 4,175,439 | A | * | 11/1979 | Laker | 73/864.72 |
| 4,418,702 | A | * | 12/1983 | Brown et al. | 128/760 |
| 4,600,507 | A | * | 7/1986 | Shimizu et al. | 422/101 X |
| 4,624,929 | A | * | 11/1986 | Ullman | 422/56 X |
| 4,774,962 | A | * | 10/1988 | Hebel et al. | 128/760 |
| 5,103,836 | A | * | 4/1992 | Goldstein et al. | 128/760 |
| 5,211,182 | A | * | 5/1993 | Deutsch et al. | 128/771 |
| 5,234,001 | A | * | 8/1993 | Goldstein et al. | 128/760 |
| 5,260,031 | A | * | 11/1993 | Seymour | 422/58 X |
| 5,283,038 | A | * | 2/1994 | Seymour | 422/58 X |
| 5,352,410 | A | * | 10/1994 | Hansen et al. | 422/58 |
| 5,468,606 | A | * | 11/1995 | Bogart et al. | 422/58 X |

FOREIGN PATENT DOCUMENTS

WO 9530484 * 11/1995

* cited by examiner

*Primary Examiner*—Arlen Soderquist

(57) ABSTRACT

Test kit whereby the sponge portion of kit is used to swab saliva. The saliva is then extracted from sponge by either squeezing it out or through the use of a centrifuge. The sponge portion of the kit is attached to a collection container when used in the centrifuge. A filter can be placed between these two portions of the kit to filter out only substances of certain molecular weights and to clean saliva. When the saliva is collected by squeezing, the sponge is placed in soft walled vial that is squeezed to extract saliva. After extracted from the sponge, the collected saliva can be removed from kit by twisting off cap. This test kit can be used for, but not limited to, testing for HIV antibodies, hepatitis and drugs.

12 Claims, 2 Drawing Sheets

SALIVA SAMPLE COLLECTION SYSTEM

CROSS-REFERENCE TO RELATED APPLICATION

This application is related to application Ser. No. 08/432,778, filed May 2, 1995, now abandoned; which was a continuation-in-part of application Ser. No. 08/239,726, filed May 9, 1994, now abandoned.

BACKGROUND OF THE INVENTION

1. Field of the Invention

The invention relates to a system for collecting and storing samples of saliva for body fluid constituent analysis.

2. Description of the Related Art

Saliva testing has recently come to the forefront as a preferred option in body fluid constituent analysis. The collection procedure is non-invasive, and saliva has been found to be a very reliable carrier of analyte indicators. For instance, PKU tests on infants are now regularly done, drug abuse is tested in many circumstances, HIV testing may be relatively reliably performed with saliva, and levels of therapeutic drugs may be ascertained through saliva testing.

A recent advance in saliva collection and test preparation is disclosed in U.S. Pat. No. 5,103,836 to Goldstein et al. An absorbent pad which is impregnated with a salt of a hypertonic solution is inserted into the mouth and saliva is brushed off from the cavity walls. After having absorbed a sufficient amount of saliva, the pad is removed and stored in a vial for later testing. The test kit is suited for immunoglobulin collection and testing for immunological information in the body fluid. That prior art test provides enough saliva for only a single test, i.e. the saliva is not collected for general, multiple testing.

Another saliva collector is disclosed in U.S. Pat. No. 5,268,148 to Seymour. A portion of filter paper is exposed so that, when enough saliva is collected, the paper will provide an indication that the collected amount is adequate.

The method and apparatus described in U.S. Pat. No. 4,774,962 to Hebel et al. allows extracting saliva from the human body in that a sponge member is chewed for a certain amount of time and after saliva has been absorbed in the sponge member, it is centrifuged therefrom. The method may be acceptable for adult saliva collection. Such a free sponge, however, is essentially unsuitable for infant testing due to the danger of ingestion and it is also not acceptable in view of the proposed utilization thereof in HIV and hepatitis testing.

The prior art devices have in common that the collection of saliva sample is rather cumbersome, it exposes the medical worker to dangerous substances, and/or the amount of saliva thus collected is inadequate to perform various tests. Also, none of the prior art devices provide a convenient method and kit for collecting large amount of saliva for body fluid constituent analysis. Finally, saliva collection from very small infants, for instance for PKU testing, is quite difficult and virtually always accompanied by forcing the infant's mouth open during the procedure.

SUMMARY OF THE INVENTION

It is accordingly an object of the invention to provide a saliva sample collection system, which overcomes the hereinafore-mentioned disadvantages of the heretofore-known devices of this general type and which provides a self-contained collection and test kit as well as a reliable and convenient method of collecting saliva samples for general, multiple testing. Finally, it is an object to provide a fully integrated, sterile package, which allows collecting and handling without any danger of exposure to the medical worker.

With the foregoing and other objects in view there is provided, in accordance with the invention, a method of collecting saliva samples for body fluid analysis. The method comprises the following steps: placing absorptive means into a patient's oral cavity and absorbing saliva into the absorptive means;

removing the absorptive means from the patient's oral cavity and placing the absorptive means into fluidic communication with a collection container.

The method is continued with a step of squeezing the saliva from the absorptive means, collecting the squeezed-out saliva at the bottom of the collection container, and then harvesting the saliva from the bottom of the container by opening a fluidic conduit at the bottom and utilizing the thus harvested saliva in a saliva testing method.

In accordance with an additional feature of the invention, the absorptive means include a cap member for placing on the collection container and fluid-tightly sealing a top of the collection container, and a sponge member for absorbing the saliva permanently attached to the cap. The sponge member is preferably formed as a pacifier nipple.

In accordance with yet another feature of the invention, the assembly includes a safety flange attached to the cap member for preventing ingestion of the absorptive means when the sponge member is placed into the patient's oral cavity. The collection assembly is quite similar to a pacifier, with the essential difference that the nipple portion is formed of absorptive material, so as to absorb saliva while the nipple placed in the patient's mouth.

In accordance with a concomitant feature of the invention, the absorptive means are impregnated with a flavor substance for stimulating a patient's saliva production. Appropriate flavors for stimulating the gland may be lemon, lime, orange, or similar flavors.

In accordance with a preferred embodiment of the invention there is provided an assembly which comprises:

absorptive means for placing into a patient's oral cavity and for absorbing saliva therein;

a collection container defining a cavity adapted to receiving the absorptive means, the collection container having resilient walls adapted to collapse towards one another upon being squeezed and to drive the saliva from the absoptive means when the absorptive means is disposed in the collection container.

In accordance with another feature of the invention, the walls of the collection container are elastically resilient.

In accordance with a final feature of the invention, the collection container further comprises a dispensing end in a vicinity of which the saliva is collected, the dispensing end having a nipple formed thereon through which the saliva is removed from the collection container.

Other features which are considered as characteristic for the invention are set forth in the appended claims.

Although the invention is illustrated and described herein as embodied in a saliva sample collection system, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of the specific embodiment when read in connection with the accompanying drawings.

DESCRIPTION OF THE PREFERRED EMBODIMENTS

Figure 1:
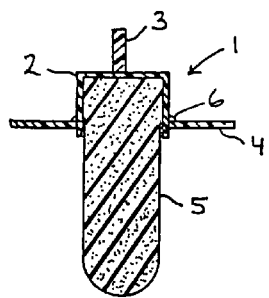
FIG. 1 is a sectional view of a cap and sponge collection assembly according to the invention.

Referring now to the figures of the drawing in detail and first, particularly, to FIG. 1 thereof, there is seen a cap and sponge assembly 1 (the collection component), which includes a cap 2, an optional handle 3, an optional safety flange 4 and a sponge 5. As will become amply clear in the following, the essential components of the assembly 1 are the cap 2 and the sponge 5. The handle 3 may be provided for easier handling of the assembly 1, and it may be integrally formed on the cap 2 or it may be glued thereon. The safety flange 4 is specifically recommended for infant testing. The safety flange 4 may be removable, and for that purpose it would be spot-welded (spot weld 6) to the cap 2 or provided with a safety ring similar to those found on plastic closures of milk jugs. Generally speaking, the cap and sponge assembly 1 is quite similar to an infant pacifier, and the assembly, and particularly the sponge 5, may be shaped in all possible pacifier shapes.

Figure 2:
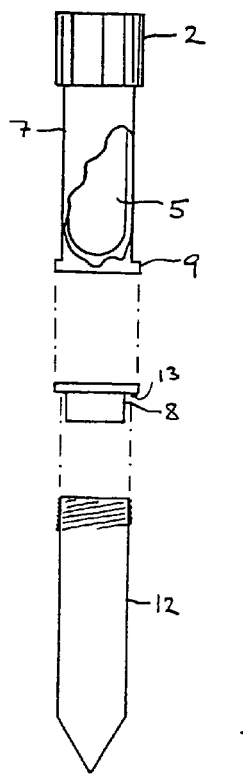
FIG. 2 is an exploded, partly broken-away, side-elevational view of a three-component assembly according to the invention.
Figure 3:
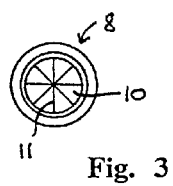
FIG. 3 is a bottom-plan view of a filter insert.
Figure 4:
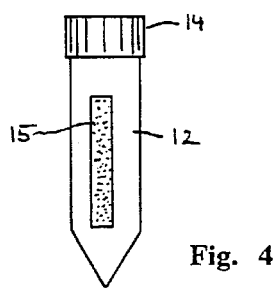
FIG. 4 is a side-elevational view of a centrifuge vial, i.e. the bottom component shown in FIG. 2, with a closure cap.

The sponge 5 is permanently locked into the inside of the cap, so as to allow a liquid-tight seal when the cap is placed on the components illustrated in FIG. 2. The sponge 5 is either polypropylene, polyethylene, polyurethane, cellulose, or blends thereof. More specifically, the sponge is formed of water-catalyzed polyurethane and more specifically it is preferably formed of HYPOL, available from Hampshire Chemical Corporation. That material has very high absorption density and excellent tensile strength. Similar materials may be used. Factors to be considered, however, are that the material must be largely inert, it must not easily break so as to prevent any ingestion of solid material, and it must have good absorptive qualities. Additionally, as will become clear from the following description, it should be able to withstand centrifugation and be able to release all or most of the saliva previously collected.

After saliva has been absorbed in the sponge 5 (after an exposure time between 20 seconds and 5 minutes in the mouth of the test patient), the cap and sponge assembly 1 is placed on a sponge holder section 7, in that the sponge 5 is inserted and the cap 2 is securely fastened thereto. A simple friction fit between the sponge holder section 7 and the cap 2 will in most cases suffice. It is also possible, however, to provide the cap 2 and the sponge holder section 7 with mutually meshing threads. The sponge holder section 7 is preferably formed as a polypropylene, polyethylene or styrene cylinder and it is provided with an attachment flange 9 at its bottom.

A filter assembly 8 is attached at the flange 9 at the bottom of the sponge holder section 7. The filter assembly is preferably attached by a substantially circumferential ultrasonic weld. The filter 8 and the sponge holder 7, therefore, form a liquid-tight seal. The filter assembly 8 has a molecular weight cut-off membrane 10 supported on a simple wire mesh 11. The membrane 10 may be adjusted to any mesh density. By way of example, a 10,000 MW (molecular weight) membrane may be used for cleaning the saliva. Other mesh sizes are also possible, depending on the specimen requirements.

A bottom stub portion of the filter assembly 8 inserts tightly into a centrifuge container 12, i.e. a saliva collection tube 12 or collection container 12. The filter 8 may come attached to the collection tube 12, so as to provide an integrated system of the components 7, 8 and 12. The filter assembly 8 may be attached to the collection tube 12 by means of a ultrasonic spot weld 13, or the like. It is important, in this respect, that the strength of the bond between the filter 8 and the collection tube 12 be smaller than that between the filter 8 and the sponge holder section 7. This ensures that, after centrifugation, the filter assembly 8 (together with the sponge holder 7 and the cap and sponge assembly 1) detaches from the collection tube 12. After separation, then, the collection tube 12 is closed and sealed with a standard threaded cap 14.

The preferred dimensions of the assembly according to the invention match those of standard centrifuge equipment. For instance, the cylindrical tubes have an outer diameter of ½ inch, the length of the collection tube is 2.125 inches, the length of the filter assembly is 5/16 of an inch and the sponge holder with the attached cap is 1.75 inches.

The collection tube 12 is also formed of a polypropylene or a similar material, and it is conical on the bottom. This facilitates sample withdrawal. The threaded cap ensures that the collected sample can be stored and shipped without drying or spilling.

A frosted area 15 may be provided on the collection tube 12, so as to allow proper labelling.

In a further embodiment, the assembly is provided for a specific test application. In that case, the bottom of the collection tube 12 holds a certain chemical reactant. When the saliva is centrifuged into contact with the reaction chemical, an indication is triggered. That indication may, for instance, be in the form of a calorimetric reaction. For that purpose it is clear that the collection tube 12 is formed of transparent or translucent material, or that a viewing window is provided. General information on saliva testing is available from "Saliva as a Diagnostic Fluid", Malamud and Tabak, Editors; Annals of the New York Academy of Sciences; Vo. 694; Sep. 20, 1993.

Figure 5:
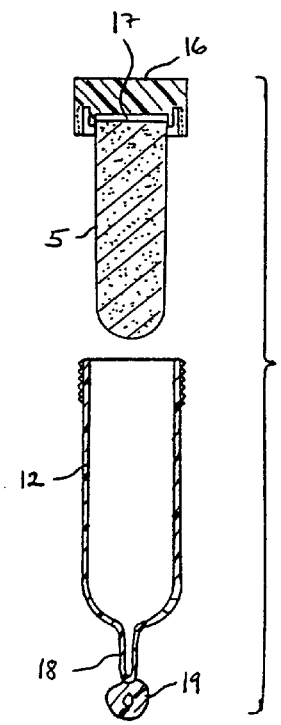
FIG. 5 is a view similar to FIG. 2 of an alternative embodiment of the invention.

With reference to FIG. 5, we have also provided a much simplified, yet integrated system for saliva collection and analysis. The embodiment is particularly based on the premise that saliva testing by colorimetry and the like has recently seen a flurry of novel developments which are all hindered by the fact that the prior art systems for collecting the saliva are typically cumbersome and slow, and/or the amount of saliva thus harvested is often not sufficient. The recent call for full disposability of such devices is answered as well with the embodiment of FIG. 5.

The nipple 5 of FIG. 5 may also be formed of HYPOL material which is directly glued to a lid 16. The adhesive connection is indicated at 17 and it is preferably formed by a LOCKTITE system (primer, accelerator, adhesive), a cyano-acrylic medical grade adhesive. The lid 16 is internally threaded so that it can be screwed onto the tube 12. In this embodiment, the tube 12 is formed of thin, i.e. squeezable material. Accordingly, when the sponge 5 is disposed in the tube 12 and the tube 12 is laterally squeezed, the saliva is driven from the sponge 5 and it collects at the bottom of the tube 12.

The bottom of the tube 12 is provided with a nipple 18. The nipple 18 can be severed (e.g. cut off with scissors) and the saliva exits from the nipple and into/onto any desired surface on which the saliva testing (e.g. HIV, Hepatitis, Drug of Abuse, PSA, etc.) may be performed. Instead of requiring a cutting tool, the nipple 18 may be provided with a twist-off cap 19.

Figure 6:
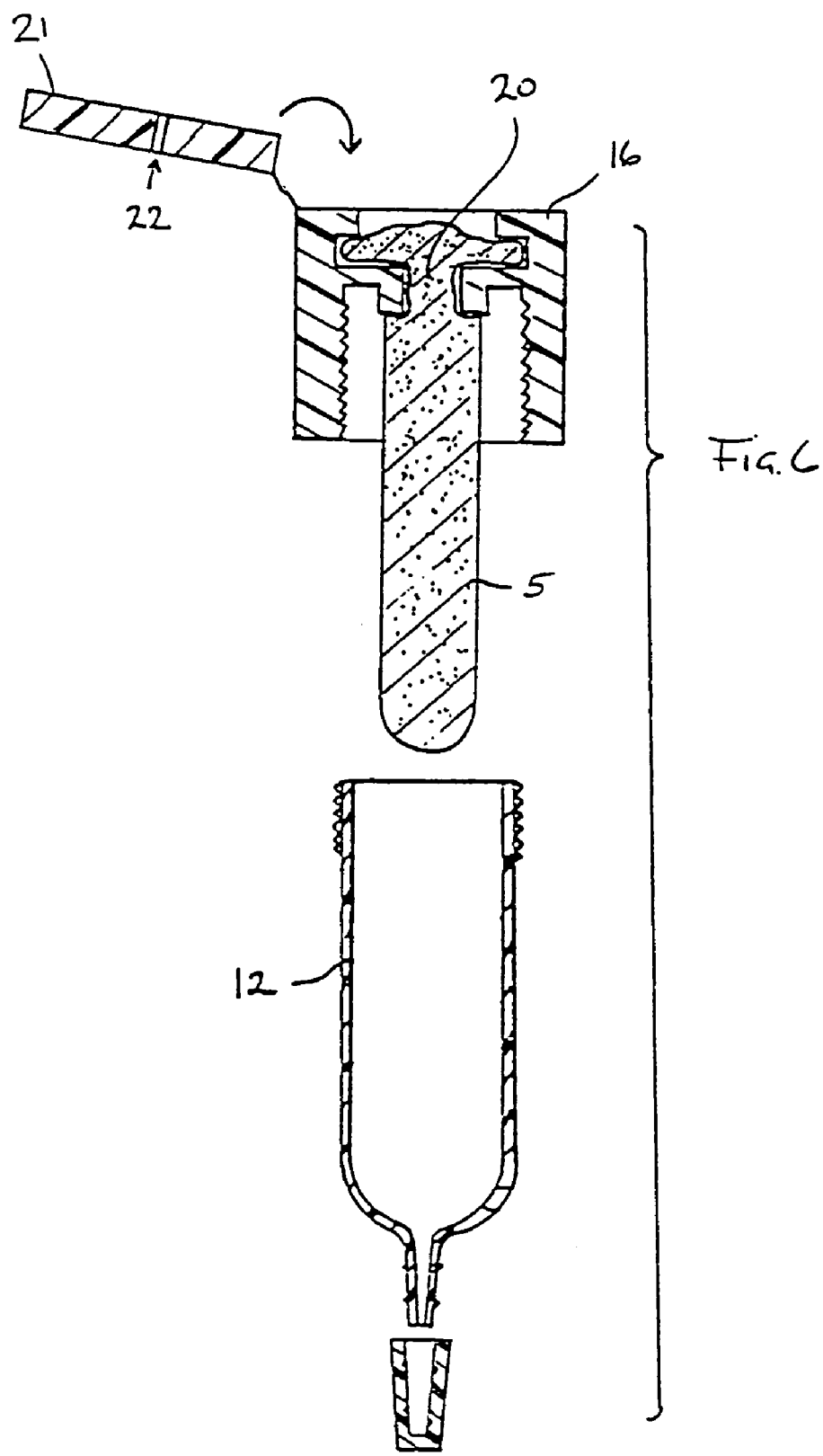
FIG. 6 is a view similar to FIG. 1 of another alternative embodiment.

With reference to FIG. 6, the sponge nipple 5 may be directly molded into the cap 16 without requiring an adhesive layer 17. In such a molding process, the directly molded foam rubber, after being molded, is allowed to vent through a casting hole vent 20. A cap plug 21, which is placed onto the cap 6 after the nipple has been molded into the cap 6, is provided with a vent opening 22 as well. A mold opening 23 in the cap 16 is undercut so as to positively and formlockingly retain the nipple 5 structure in the cap 16.

The invention claimed is:

1. A method of collecting saliva samples for body fluid analysis, which comprises:

placing absorptive means comprising a sponge member for absorbing the saliva, said sponge member being permanently attached to a cap member, into a patient's oral cavity, the sponge member extending into said oral cavity and the cap member remaining outside said oral cavity, and absorbing saliva into the absorptive means;

removing the absorptive means from the patient's oral cavity and placing the absorptive means into fluidic communication with a collection container; and driving the saliva from the absorptive means and collecting the saliva in the collection container, by squeezing the collection container for indirectly squeezing the saliva out of the absorptive means and into the collection container.

2. The method according to claim 1, wherein the step of placing comprises placing absorptive means selected from the group consisting of polyurethane, polyethylene, polypropylene, and cellulose.

3. An assembly for collecting saliva for body fluid analysis, comprising:

absorptive means for placing into a patient's oral cavity, comprising a sponge member for absorbing the saliva, said sponge member being permanently attached to a cap member, the sponge member extending into said oral cavity and the cap member remaining outside said oral cavity, and for absorbing saliva therein;

a collection container defining a cavity adapted to receive said sponge member; said collection container having resilient walls adapted to collapse towards one another upon being squeezed and to drive the saliva from said absorptive means when said absorptive means is disposed in said collection container.

4. The assembly according to claim 3, wherein said walls of said collection container are elastically resilient.

5. The assembly according to claim 3, wherein said collection container further comprises a dispensing end in a vicinity of which the saliva is collected, said dispensing end having a nipple formed thereon through which the saliva is removed from said collection container.

6. The assembly according to claim 3, wherein said absorptive means are formed of a material selected from the group consisting of polyurethane, polyethylene, polypropylene, and cellulose.

7. The assembly according to claim 3, wherein said absorptive means are formed from water-catalyzed polyurethane.

8. The assembly according to claim 3, wherein said cap member is adapted for placing on said collection container and fluid-tightly sealing a top of said collection container section.

9. The assembly according to claim 8, wherein said sponge member is formed as a pacifier nipple.

10. The assembly according to claim 9, including a safety flange attached to said cap member for preventing ingestion of said absorptive means when said sponge member is placed into the patient's oral cavity.

11. The assembly according to claim 3, wherein said absorptive means are impregnated with a flavor substance for stimulating a patient's saliva production.

12. The assembly according to claim 3, which further comprises a chemical test reagent disposed in said collection container.

* * * * *